United States Patent
Anderson

(10) Patent No.: US 10,595,850 B2
(45) Date of Patent: Mar. 24, 2020

(54) SUTURE ASSEMBLY WITH SUTURE LOAD DISTRIBUTION

(71) Applicant: Biomet C.V., Warsaw, IN (US)

(72) Inventor: David Anderson, Winona Lake, IN (US)

(73) Assignee: Biomet C.V., Warsaw, IN (US)

( * ) Notice: Subject to any disclaimer, the term of this patent is extended or adjusted under 35 U.S.C. 154(b) by 276 days.

(21) Appl. No.: 15/838,931

(22) Filed: Dec. 12, 2017

(65) Prior Publication Data

US 2018/0193013 A1 Jul. 12, 2018

Related U.S. Application Data

(62) Division of application No. 14/176,804, filed on Feb. 10, 2014, now Pat. No. 9,872,677.

(51) Int. Cl.
| | |
|---|---|
| *A61B 17/04* | (2006.01) |
| *B60C 9/00* | (2006.01) |
| *D01D 10/02* | (2006.01) |
| *D01F 6/62* | (2006.01) |

(52) U.S. Cl.
CPC ........ *A61B 17/0401* (2013.01); *B60C 9/0042* (2013.01); *D01D 10/02* (2013.01); *D01F 6/62* (2013.01); *A61B 2017/0403* (2013.01); *A61B 2017/0406* (2013.01); *A61B 2017/0417* (2013.01); *A61B 2017/0495* (2013.01)

(58) Field of Classification Search
CPC ........ A61B 17/0401; A61B 2017/0403; A61B 2017/0406; A61B 2017/0417; A61B 2017/0495

See application file for complete search history.

(56) References Cited

U.S. PATENT DOCUMENTS

| | | | |
|---|---|---|---|
| 5,540,718 A | 7/1996 | Bartlett | |
| 8,932,331 B2 * | 1/2015 | Kaiser | A61B 17/0401 606/232 |
| 2013/0035698 A1 | 2/2013 | Stone | |
| 2013/0296893 A1 | 11/2013 | Dean et al. | |
| 2014/0155938 A1 | 6/2014 | Anderson | |

OTHER PUBLICATIONS

"U.S. Appl. No. 14/176,804, Final Office Action dated Jun. 5, 2017", 11 pgs.
"U.S. Appl. No. 14/176,804, Non Final Office Action dated Oct. 5, 2016", 10 pgs.
"U.S. Appl. No. 14/176,804, Notice of Allowance dated Sep. 14, 2017", 12 pgs.
"U.S. Appl. No. 14/176,804, Response filed Feb. 1, 2017 to Non Final Office Action dated Oct. 5, 2016", 10 pgs.
"U.S. Appl. No. 14/176,804, Response filed Aug. 7, 2017 to Final Office Action dated Jun. 5, 2017", 10 pgs.

* cited by examiner

*Primary Examiner* — Ashley L Fishback
(74) *Attorney, Agent, or Firm* — Schwegman Lundberg & Woessner, P.A.

(57) ABSTRACT

A method for securing a flexible member may include forming a bore in a bone; inserting an anchor into the bore, the anchor including a passage and being coupled to a flexible member; slideably positioning a first load distributing member along the flexible member; inserting the first load distributing member into the bore such that the flexible member engages the first load distributing member; and applying tension to a portion of the flexible member to secure the anchor and load distributing member within the bone.

18 Claims, 7 Drawing Sheets

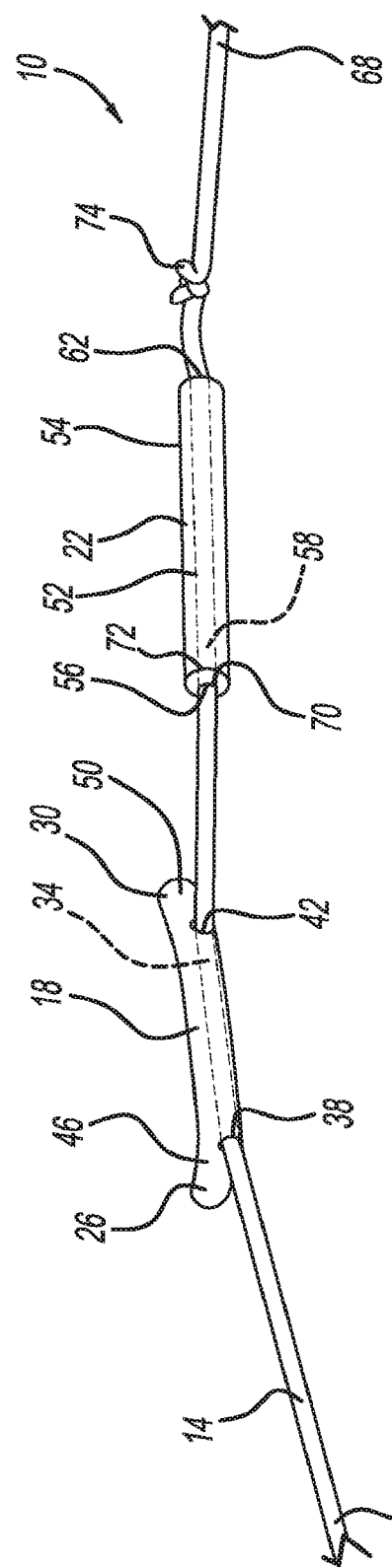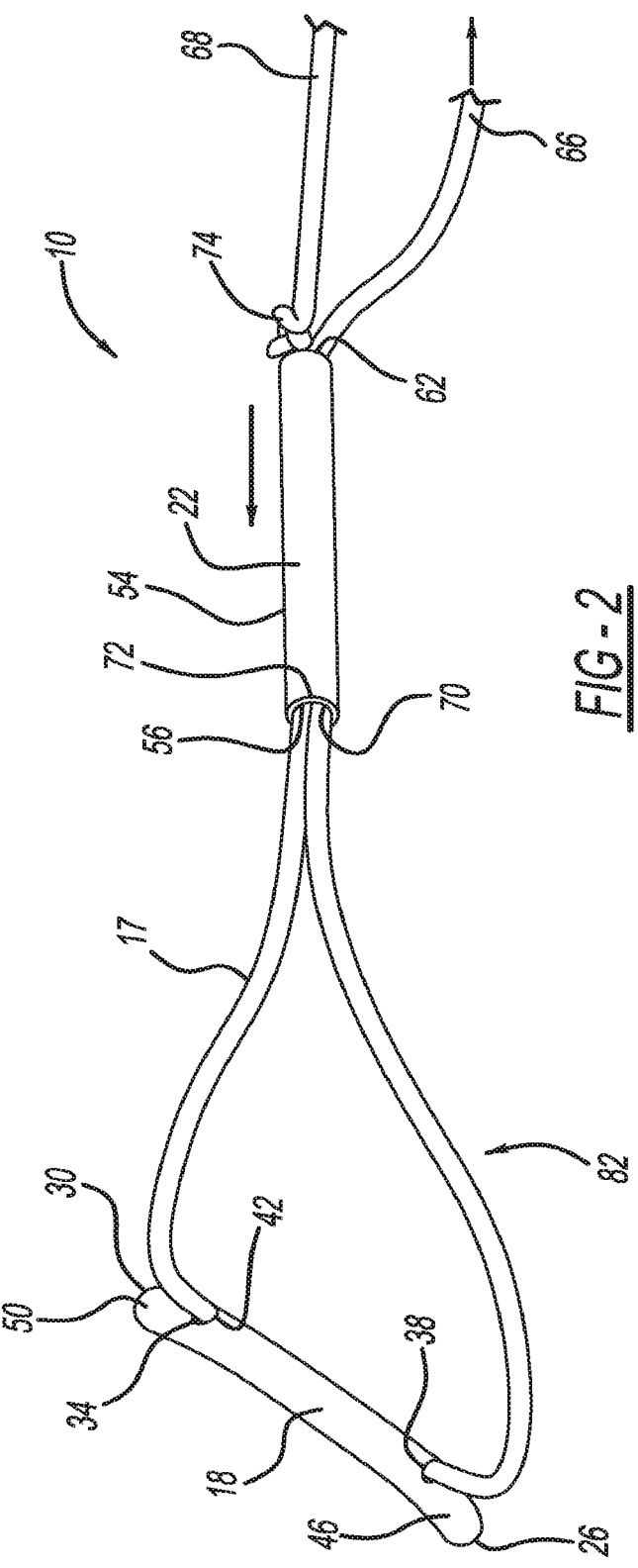

SUTURE ASSEMBLY WITH SUTURE LOAD DISTRIBUTION

PRIORITY APPLICATIONS

This application is a divisional application of U.S. patent application Ser. No. 14/176,804, filed Feb. 10, 2014, the content of which is incorporated herein by reference in its entirety.

FIELD

The present disclosure relates generally to a method and apparatus for attaching bones and/or soft tissue.

BACKGROUND

This section provides background information related to the present disclosure which is not necessarily prior art.

Breaks in bone or soft tissue damage due to injury can be repaired by suturing. Various repair techniques and devices have been developed for facilitating suturing that include the use of sutures contacting the bone. Sutures, when used to stabilize tissue or bone portions together, are under tensile force and apply force to the bone or soft tissue portion. Often the suture may rub against the bone and may cause the bone to be cut or fracture or the suture to fray.

There is a need in the relevant art for bone and soft tissue repair techniques and associated devices for facilitating suturing without damage to the bones, soft tissue or the sutures.

SUMMARY

This section provides a general summary of the disclosure, and is not a comprehensive disclosure of its full scope or all of its features.

In an example embodiment, a method for securing a flexible member may include forming a bore in a bone; inserting an anchor into the bore, the anchor including a passage and being coupled to a flexible member; slideably positioning a first load distributing member along the flexible member; inserting the first load distributing member into the bore such that the flexible member engages the first load distributing member; and applying tension to a portion of the flexible member to secure the anchor and load distributing member within the bone.

In another embodiment, a method for securing a flexible member may include forming a first bore in a first portion of bone; forming a second bore in a second portion of bone; inserting a first anchor into the first bore and a second anchor into the second bore; positioning a first load distributing element relative to the first bore; positioning a second load distributing element relative to the second bore, wherein the first and second load distributing elements are slideably engaged to a flexible member; and applying tension to a portion of the flexible member to secure the first and second load distributing elements and first and second anchors within the first and second bores, respectively.

In an example embodiment a suture assembly may include a flexible member. An anchor defines a passage and is slideably coupled to the flexible member. A first load distributing member may be disposed along the flexible member. A retaining element is positioned on the flexible member adjacent to the first load distributing member. The retaining element adjusts the position of the first load distributing member on the flexible member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of a suture construct according to the present disclosure;

FIG. 2 is another perspective view of the suture construct of FIG. 1 above forming a loop;

Corresponding reference numerals indicate corresponding parts throughout the several views of the drawings.

DETAILED DESCRIPTION

Figure 3:
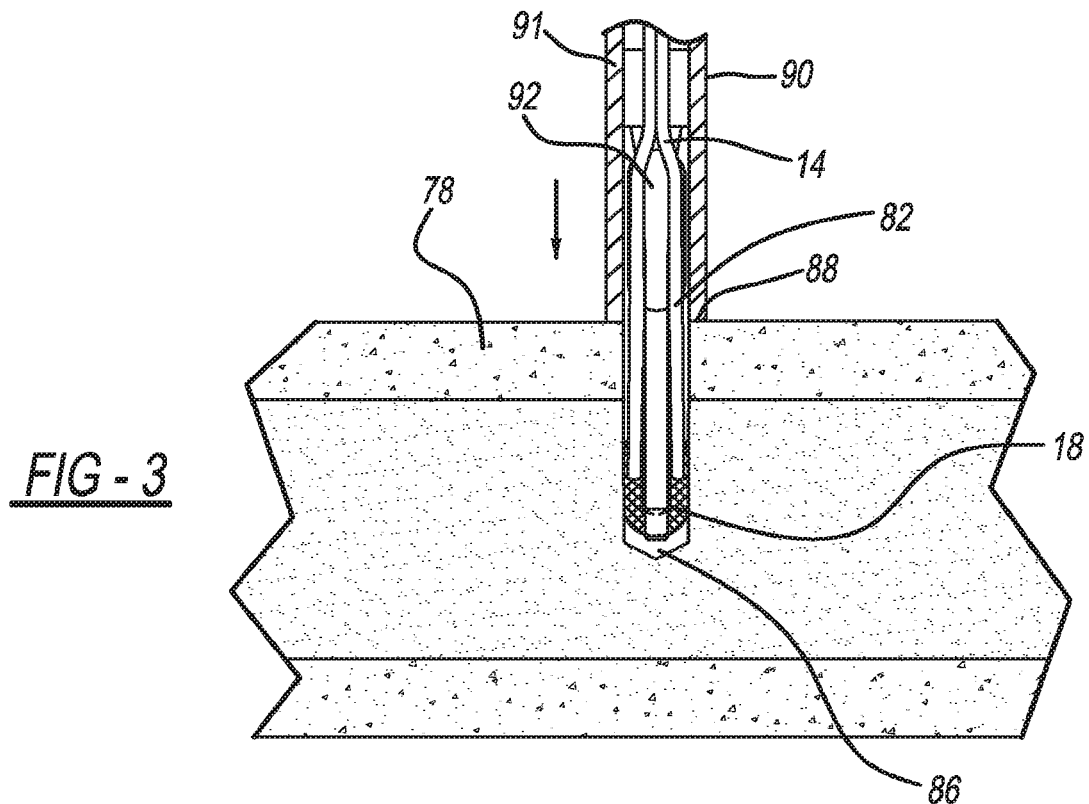
FIG. 3 is an environmental view of the suture construct of FIG. 1 being inserted in a bone with a bone insertion tool.

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom.

The present technology generally relates to instruments useful for attaching bones or bone fragments and methods for improving the procedures for attaching bones or bone fragments. As used herein, the term "suture construct" and "suture assembly" may be used to refer to an entire suture construct, or a portion thereof; portions may be as large or as small as necessary to accommodate the specific need. For example, a suture construct made in accordance with the present disclosure may constitute the entire suture construct, or it may be used with one or more pieces or components that together form a final suture construct or suture assembly.

The present disclosure encompasses a wide variety of therapeutic and cosmetic applications, for human and/or other animal subjects, and the specific materials, devices, and instruments used should be biomedically acceptable. As used herein, such a "biomedically acceptable" or "biocompatible" material or component is one that is suitable for use with humans and/or animals without undue adverse side effects (such as toxicity, irritation, and allergic response) commensurate with a reasonable benefit/risk ratio.

The terminology used herein is for the purpose of describing particular example embodiments only and is not intended to be limiting. In this disclosure, the terms "anterior," "posterior," "lateral," and "medial" generally refer to the front, back, outside, and midline of a surgical patient, respectively, although these terms are also used in reference to instruments and/or devices. It should also be noted that the term "user" may refer to a surgeon or any one of a number of individuals who assist the surgeon during a procedure. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance.

With initial reference to FIGS. 1-12, various methods and apparatus are disclosed for attaching bones, bone fragments, and soft tissue to bones. With particular reference to FIG. 1, a suture construct or suture assembly 10 includes a suture 14, at least one anchor 18, and at least one load distributing element 22. Anchor 18 may be a soft, flexible or deformable anchor of the type disclosed in U.S. Publication 2011/0098727, which is incorporated by reference herein in its entirety. Anchor 18 may be an elongate member having a sleeve or tubular configuration with first and second ends 26, 30 and an internal passage 34 extending therebetween. Anchor 18 may be comprised of resorbable or non-resorbable materials, including braided suture, sponges and sponge-like materials in solid form, perforated materials, woven/braided from biocompatible materials or fibers, such as, for example, polymer, polyester, polyethylene, cotton, silk, or other natural or synthetic materials.

Anchor 18 may have any properties that allow anchor 18 to change shape or deform. In this regard, anchor 18 can be, for example, compliant, flexible, foldable, squashable, squeezable, deformable, limp, flaccid, elastic, low-modulus, soft, spongy or perforated, or have any other characteristic property that allows it to change shape. In some aspects, anchor 18 can be coated with biological or biocompatible coatings, and also can be soaked in platelets and other biologics, which can be easily absorbed by anchor 18. In one exemplary configuration, anchor 18 can be formed from a strand of No. 5 braided polyester suture. In other words, multiple fibers can be braided together to form a hollow braided suture having a longitudinal passage 34.

As shown for example in FIGS. 1 and 2, suture 14 can be passed through a first opening 38 in a wall of anchor 18, guided into and along a portion of passage 34, and passed out of passage 34 through a second opening 42 in the wall of anchor 18. Openings 38, 42 can be positioned intermediately between first and second ends 26, 30 of anchor 18 at a distance of, for example, one-quarter length from ends 26, 30. It will be appreciated that openings 38, 42 can be apertures or voids in the woven fabric of anchor 18, such that openings 38, 42 do not disrupt or break the weave of anchor 18 when made of braided or woven material. Further, portions of anchor 18 between first and second ends 26, 30 and corresponding first and second openings 38, 42, can define anchoring legs or tail portions 46, 50 that can provide additional resistance for securing anchor 18 relative to the bone. In one exemplary configuration, suture 14 can pass only through openings 38, 42 and a portion of passage 34 extending therebetween to form a loop that does not extend through tail portions 46, 50.

While anchor 18 is illustrated and described as a flexible anchor, it is understood that anchor 18 may also be a rigid anchor of the type disclosed in U.S. Pat. No. 7,713,285 and U.S. Publication No. 2011/0208240, which are incorporated by reference herein in their entirety, or any other type of rigid anchor.

At least one load distributing element 22 may be of a cylindrical or tubular shape and may be positioned along suture 14. Load distributing element may include an elongated cylindrical bore 52 and an outer cylindrical wall 54. Load distributing element 22 may be of a rigid material (for example only, polyester, PEEK, PEKK, or other biocompatible material; stainless steel; or titanium/titanium alloy,) and may distribute load created through tensioning suture 14 across a bone or soft tissue. Load distributing element 22 may have properties that allow load distributing element 22 to retain its shape in various environments. In this regard, load distributing element 22 can be, for example, rigid, unbending, inflexible, stiff, firm, unyielding, inelastic, or have any other characteristic property that allows it to retain its shape. In one exemplary configuration, load distributing element 22 can be formed from polyester.

Further, in other embodiments, load distributing element 22 may also be of a flexible material allowing load distributing element 22 to change shape. In this regard, load distributing element 22 can be, for example, compliant, flexible, foldable, squashable, squeezable, deformable, limp, flaccid, elastic, low-modulus, soft, spongy or perforated, or have any other characteristic property that allows it to change shape. In one exemplary configuration, load distributing element 22 can be formed from a strand of braided polyester suture. In other words, multiple fibers can be braided together to form a hollow braided suture having a longitudinal passage.

As shown, for example, in FIG. 1, suture 14 can be passed through a first opening 56 in load distributing element 22, guided into and along elongated cylindrical passage 58, and passed out of passage 58 through a second opening 62 in load distributing element 22 to form suture construct 10 having free ends 66 and 68. Load distributing element 22 may be slideable along suture 14 and a diameter of bore 52 may be sized to receive multiple lengths of suture 14 such as two lengths. A diameter of cylindrical wall 54 may be sized to snugly engage with a wall of a bore, which is described in further detail below.

Figure 6:
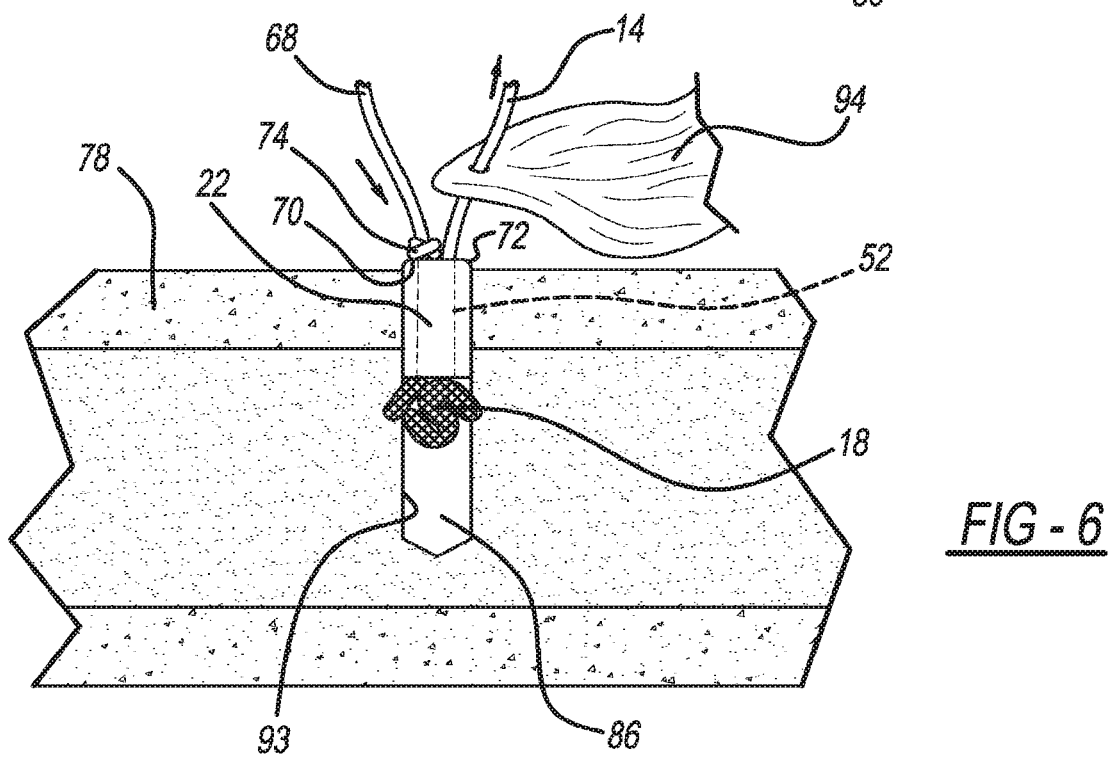
FIG. 6 is an environmental view of the suture construct of FIG. 1 secured within the bone and a load distributing element inserted within the bone.

Bore 52 includes edges 70 and cylindrical wall 54 includes edges 72 at openings 56, 62 of load distributing element. Edges 70, 72 may be rounded or chamfered to prevent fraying or breaking of suture 14 if the load distributing element 22 is made of a relatively rigid material, as shown in FIG. 6. A length of the load distributing element 22 may be sized such that load distributing element 22 protrudes from the bore or is flush with the top of the bore, also discussed further below.

Load distributing element 22 may be placed along suture 14 to protect suture 14 from the environment and/or to protect bones or soft tissue in the environment from being damaged by suture 14. In an exemplary embodiment, load distributing element 22 may be placed within an aperture in a bone to protect the bone from being cut or fractured (for example only in small bones such as the phalanges in the foot) by suture 14 and protect suture 14 from breakage or fraying from the bone, as discussed further below. Load distributing element 22 also protects soft tissue from being cut by suture 14 when being secured to a bone, such as in a rotator cuff repair. In another embodiment, load distributing element 22 may be placed on a flat surface of bone to prevent suture 14 from wearing away a portion of the bone and to distribute loads from the suture on the bone, as discussed further below. In still other embodiments, load distributing element 22 may be used with soft tissue to prevent suture 14 from cutting the soft tissue, as discussed further below.

A retaining element 74 may be placed on suture 14 near load distributing element 22 and at one end 68 of the suture 14. In one exemplary configuration, retaining element 74 may be a knot in the suture 14. In other embodiments, retaining element 74 may be a crimp, a clamp, a separate material, or any other structure that prevents load distributing element 22 from passing over or going past retaining element 74 and along suture 14.

Now referring additionally to FIG. 2, the assembled suture construct 10 is illustrated. End 66 is passed through passage 58 in load distributing element 22 and passage 34 in anchor 18. Retaining element 74 is placed in suture 14 between load distributing element 22 and end 68. End 66 is fed back through passage 58 in load distributing element 22 such that both ends 66 and 68 are on the same side of load distributing element 22 and an adjustable loop 82 is created in suture 14 on the opposite side of load distributing element 22.

Now referring to FIGS. 3-6, an illustration of suture assembly 10 in an exemplary bone, such as a humerus, for attaching soft tissue such as a rotator cuff is illustrated. A blind bore 86 having an edge 88 is formed in bone 78 such as by drilling or punching. Loop 82 in suture 14, and specifically anchor 18, is inserted into bore 86 using bone insertion tool 90. Bone insertion tool 90 includes both a tubular guide or cannula 91 and a driver or pusher 92 and may be any tool known, such as the bone insertion tool disclosed in U.S. Publication 2011/0098727, which is incorporated herein by reference in its entirety.

Figure 4:
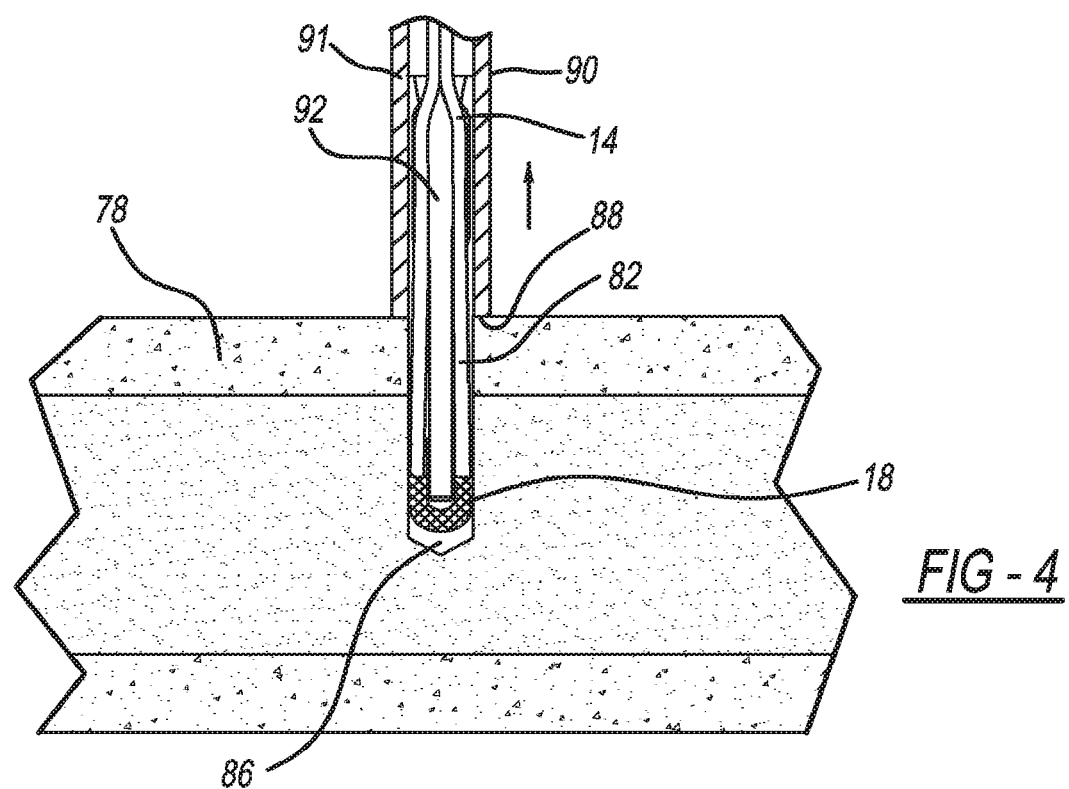
FIG. 4 is an environmental view of the suture construct of FIG. 1 inserted into the bone.
Figure 5:
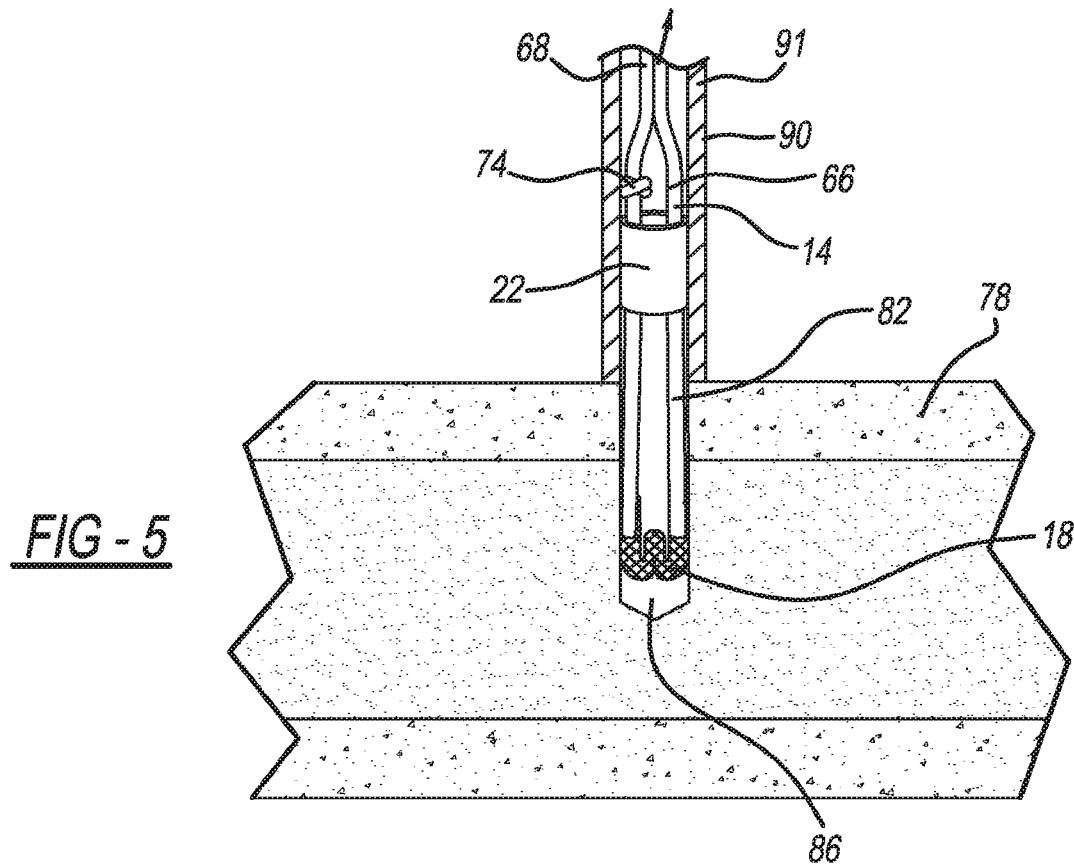
FIG. 5 is an environmental view of the tool being removed from the suture construct of FIG. 1.

Referring specifically to FIG. 3, bone insertion tool 90 pushes anchor 18 to a base of bore 86 in bone 78. Guide 91 directs the suture assembly 10 and the driver 92 into the bore 86. In FIG. 4, driver 92 is being removed from bore 86, leaving only the suture assembly 10 and the guide 91. As driver 92 is removed from bore 86, end 66 of suture 14 is pulled removing slack in suture 14 between retaining element 74, load distributing element 22, and anchor 18, thereby drawing the ends of each together as illustrated in FIGS. 5-6.

As end 66 is pulled, the diameter of retaining element 74 is larger than the diameter of passage 58 in load distributing element 22 and prevents suture 14 beyond load distributing element 22 from being pulled through passage 58 in load distributing element 22. Retaining element 74 thus causes load distributing element 22 to move and be guided down guide 91 towards bore 86 and be automatically slideably inserted into bore 86 only by tensioning end 66 of suture 14. Alternatively, while load distributing element 22 can be automatically pulled into bore 86 only by tensioning end 66 of the suture assembly 10, load distributing element 22 may also be manually inserted or pushed into the bore before tensioning the suture assembly 10 by pulling end 66 of suture 14. Once inserted in bore 86, load distributing element 22 fits snugly within bore 86 and is retained within bore 86 by retaining element 74 and anchor 18.

With continued reference to FIG. 6, the length of load distributing element 22 is such that when inserted within bore 86, a portion of load distributing element 22 protrudes from bore 86. Load distributing element 22 may protrude from bore 86 to keep suture 14 from contacting bone 78 along edge 88 of bore 86. As suture 14 enters and exits load distributing element 22 near edge 88 of bore 86, suture 14 contacts edge 70 and perhaps edge 72 of the load distributing element 22 instead of edge 88 of bore 86 to avoid cutting bore 86 of bone 78. Edges 72, 72 of first and second openings 56 and 62 of load distributing element 22 are chamfered or rounded to prevent fraying or breaking of suture 14 as force is applied on the edges of first and second openings 56 and 62 from the suture 14.

Further, as end 66 is pulled to tension suture assembly 10, anchor 18 changes from a first shape to a second shape within bore 86 applying a compressive force against a wall 93 of bore 86 and securing anchor 18 within bore 86. Tail portions 46, 50 of anchor 18 provide additional resistance against the wall 93 of bore 86 for securing anchor 18 relative to bone 78. Thus, when anchor 18 is secured within bore 86 and load distributing element 22 is inserted within bore 86, suture assembly 10 is fixed within bore 86 and exits bore 86 through load distributing element 22 which protects bone 78 from cutting or fracture caused by suture 14 (see FIG. 6). Suture 14 is also protected from breaking or fraying caused by bone 78.

With continuing reference to FIG. 6, a portion of soft tissue 94 may be fastened to the bone 78 such as for a rotator cuff repair. One or both ends 66, 68 may be inserted through the tissue 94 and knotted to secure the tissue 94 to the bone 78. If only one end 66 is inserted through the tissue, end 66 may be tied to end 68 to secure the tissue 94 to the bone 78. Tissue 94 may extend up to, cover, or be away from bore 86. In some embodiments, load distributing element 22 may extend through tissue 94 to prevent suture 14 from cutting tissue 94. In alternative embodiments, load distributing element 22 may not extend through tissue 94. While FIG. 6 depicts ends 66 and 68 attaching tissue 94 to bone 78, in other embodiments ends 66 and 68 may fasten another portion of bone to bone 78 (as discussed in further detail below).

Figure 7:
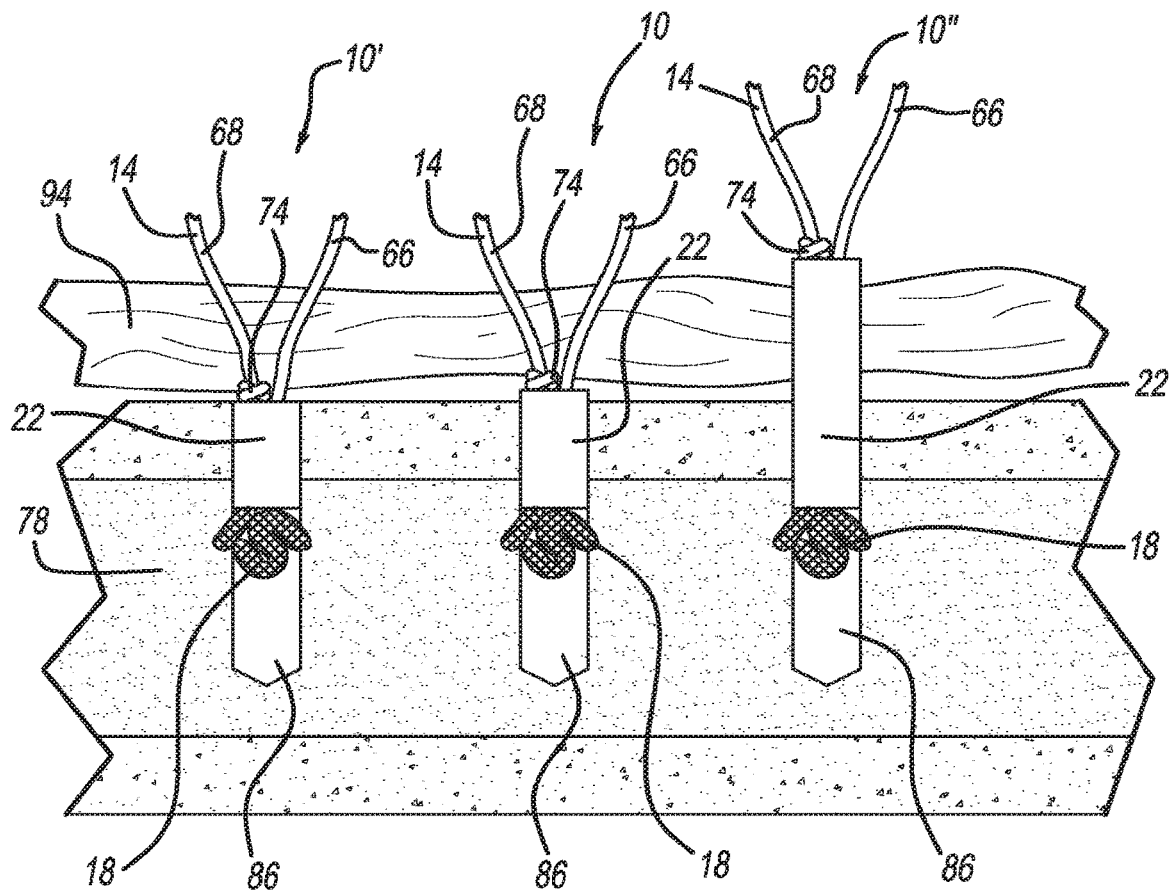
FIG. 7 is an environmental view of the suture construct of FIG. 1 above securing tissue to a bone.

Now referring to FIG. 7, an illustration of a plurality of suture assemblies 10, 10', 10" in an exemplary bone, such as a humerus, for attaching soft tissue such as a rotator cuff is illustrated. The plurality of suture constructs 10, 10', 10" may be inserted into a plurality of bores 86 in bone 78 to fasten tissue 94 to bone 78. Load distributing element 22 may protrude into at least one of bore 86 and tissue 94 to protect bone 78 from fracture or cutting and tissue 94 from cutting from suture 14. In some embodiments, some of the plurality of load distributing elements 22 may protrude through both bone 78 and tissue 94, and the remainder of load distributing elements 22 may protrude only through bone 78. Suture constructs 10, 10', 10" are inserted into bone 78 in the method described relating to FIGS. 1-6. Once suture constructs 10, 10', 10" are secured in bone 78, tissue 94 is placed on bone 78 and attached using ends 66 and 68 as discussed in relation to FIG. 6. In some embodiments, suture assemblies 10, 10', 10" may be secured individually and remain individual suture assemblies 10, 10', 10". In other embodiments, suture assemblies 10, 10', 10" may be linked or tied/knotted together forming a daisy chain of suture assemblies 10, 10', 10". In these embodiments, additional load distributing elements 22 may be added to the suture assemblies 10, 10', 10" to prevent cutting of the tissue.

Figure 8:
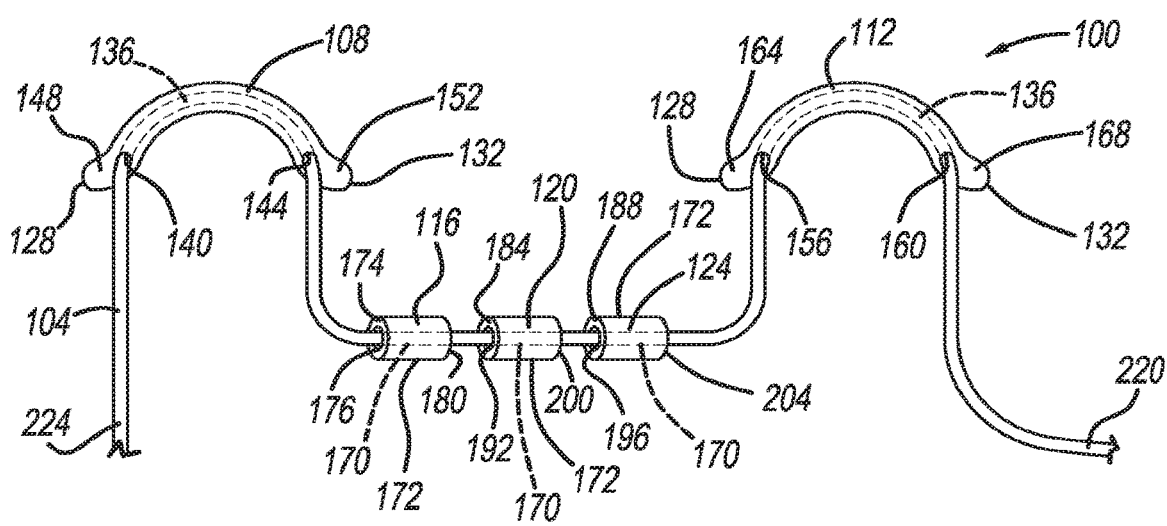
FIG. 8 is a perspective view of another embodiment of a suture construct according to the present disclosure.

Referring to FIGS. 8-12, another method and apparatus is disclosed for attaching bone or bone fragments. While the previous embodiment is primarily used to attach soft tissue to bone, the embodiment of FIGS. 8-12 can be used for attaching a plurality of bones or portions of bones. Referring specifically to FIG. 8, a suture construct, or suture assembly, 100 may include a suture 104, a plurality of anchors 108, 112 (for example only, two), and a plurality of load distributing elements 116, 120, 124 (for example only, three). Anchors 108, 112 and load distributing elements 116, 120, 124 may be substantially similar to anchor 18 and load distributing element 22 of FIG. 2. Anchors 108, 112 may include first and second ends 128, 132 and an internal passage 136 extending therebetween.

As shown in FIGS. 8-11, anchor 108 further includes a first opening 140 and a second opening 144 with passage 136 extending therebetween. Openings 140, 144 can be positioned intermediately between first and second ends 128, 132 of anchor 108 at a distance of, for example, one-quarter length from ends 128, 132. Further, portions of anchor 108 between first and second ends 128, 132 and corresponding first and second openings 140, 144, can define anchoring leg or tail portions 148, 152. In one exemplary configuration, passage 136 does not extend through tail portions 148, 152.

Similarly to anchor 108, anchor 112 further includes a first opening 156 and a second opening 160 with passage 136 extending therebetween. Openings 156, 160 can be positioned intermediately between first and second ends 128, 132 of anchor 112 at a distance of, for example, one-quarter length from ends 128, 132. Further, portions of anchor 112 between first and second ends 128, 132 and corresponding first and second openings 156, 160, can define anchoring leg or tail portions 164, 168. In one exemplary configuration, passage 136 does not extend through tail portions 164, 168.

While anchors 108, 112 are illustrated and described as flexible anchors, it is understood that at least one or portions of the anchors 108, 112 may also be a rigid anchor.

Load distributing elements 116, 120, 124 may be of a cylindrical or tubular shape and may each include an elongated cylindrical bore 170 and a cylindrical wall 172. Load distributing element 116 further includes a first opening 174 and a second opening 180 with a passage 176 extending therebetween. Load distributing element 116 may be placed along suture 104 to protect suture 104 from the environment and/or to protect bones or soft tissue in the environment from being damaged by suture 104. Load distributing element 116 is slideable along suture 104. A diameter of elongated cylindrical bore 170 is sized to receive multiple lengths of suture 104. A diameter of cylindrical wall 172 is sized to snugly engage with a wall of a bore, which is described in further detail below. A length of load distributing element 116 may be sized such that load distributing element 116 protrudes from the bore or is flush with the top of the bore, also discussed further below.

Similarly to load distributing element 116, load distributing elements 120 and 124 further include first openings 184, 188 and second openings 200, 204 with passages 192, 196 extending therebetween. Load distributing elements 120, 124 may be placed along suture 104 to protect suture 104 from the environment and/or to protect bones or soft tissue in the environment from being damaged by suture 104. Load distributing elements 120, 124 are slideable along suture 104 and have inner diameters sized to receive two lengths of suture 104. Load distributing elements 120, 124 also have outer diameters sized to snugly engage with a wall of a bore, which is described in further detail below. Lengths of load distributing elements 120, 124 may be sized such that load distributing elements 120, 124 protrudes from the bore or are flush with the top of the bore, also discussed further below. Lengths of load distributing elements 120, 124 may also be sized such that load distributing elements 120, 124 may be placed on a surface of bone or tissue to prevent suture 104 from contacting the bone or tissue and distribute load more evenly across the surface of the bone or tissue, as discussed further below.

Figure 10:
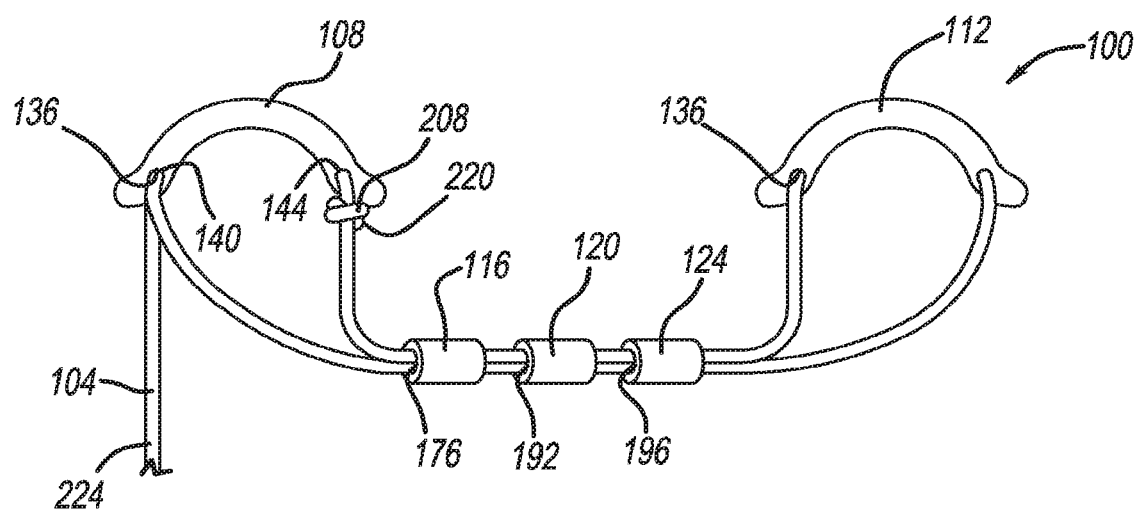
FIG. 10 is a perspective view of the assembled suture construct of FIG. 8.
Figure 11:
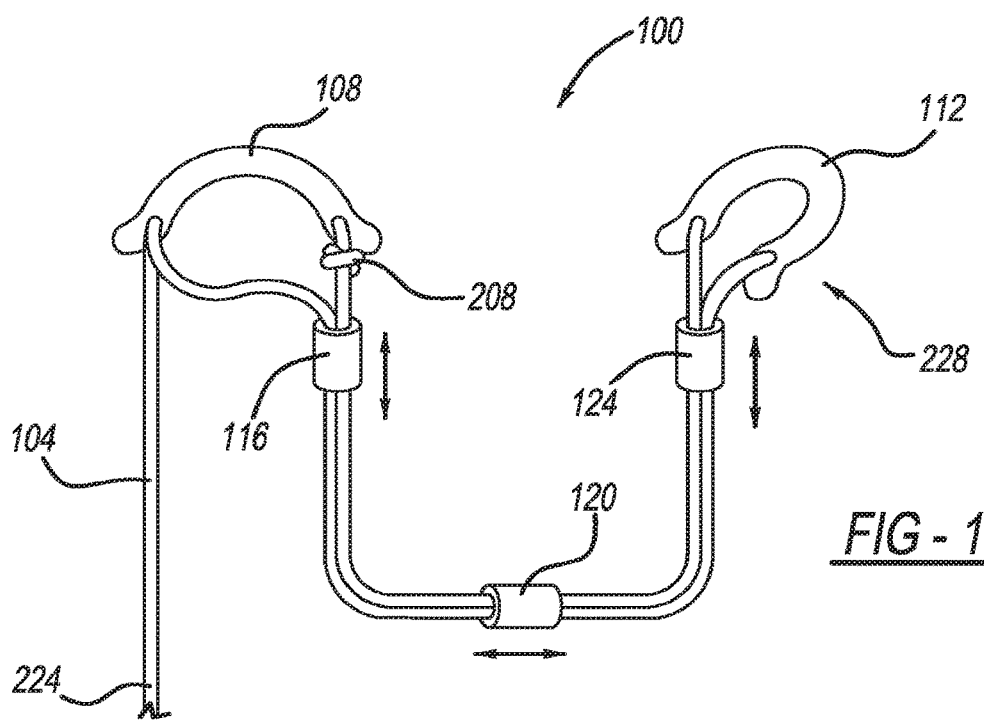
FIG. 11 is a perspective view of the assembled suture construct of FIG. 8 with load distribution elements placed strategically along the suture construct.

Now with reference to FIGS. 10-11, a retaining element 208 may be placed on suture 104 near opening 144 of anchor 108. In one exemplary configuration, retaining element 208 may be a knot in suture 104. In other embodiments, retaining element 208 may be a crimp, a clamp, a separate material, or any other structure that prevents load distributing element from passing over retaining element 208 and along suture 104.

Figure 9:
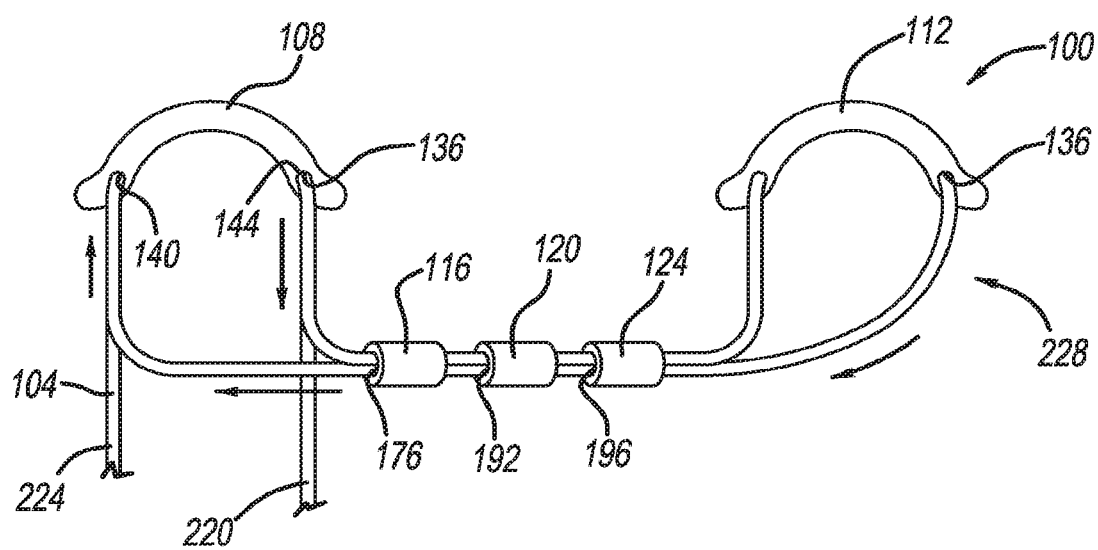
FIG. 9 is a perspective view of the assembly of the suture construct of FIG. 8 above forming a loop.

Now referring additionally to FIGS. 9-11, the assembly of suture construct 100 is illustrated. End 220 of suture 104 is passed through passage 136 in anchor 108, through passages 176, 192, 196 in load distributing elements 116, 120, 124, and though passage 136 in anchor 112 (see FIG. 8). As best illustrated in FIG. 9, end 220 is fed back through passages 196, 192, 176 in load distributing elements 124, 120, 116 such that both ends 220, 224 are on the same side of load distributing elements 116, 120, 124 and a loop 228 is created in suture 104 on the opposite side of load distributing elements 116, 120, 124.

With continuing reference to FIGS. 9 and 10, end 220 is fed back through passage 136 in flexible anchor 108, in through opening 140 and out through opening 144, such that suture 104 passes through passage 136 in the same direction as suture 104 passed through passage 136 initially. Retaining element 208 is placed in suture 104 between flexible anchor 108 and load distributing element 116. Retaining element 208 is formed by knotting end 220 to suture 104 between flexible anchor 108 and load distributing element 116 (FIG. 10).

Now referring to FIG. 11, load distributing elements 116 and 124 are slideably positioned along suture 104 near anchors 108 and 112. Load distributing element 120 is slideably positioned half way between load distributing anchors 116 and 124 in preparation for insertion into bone and/or tissue. End 224 remains free to enable tensioning of suture assembly 100 once suture assembly 100 is positioned within bone and/or tissue.

Figure 12A:
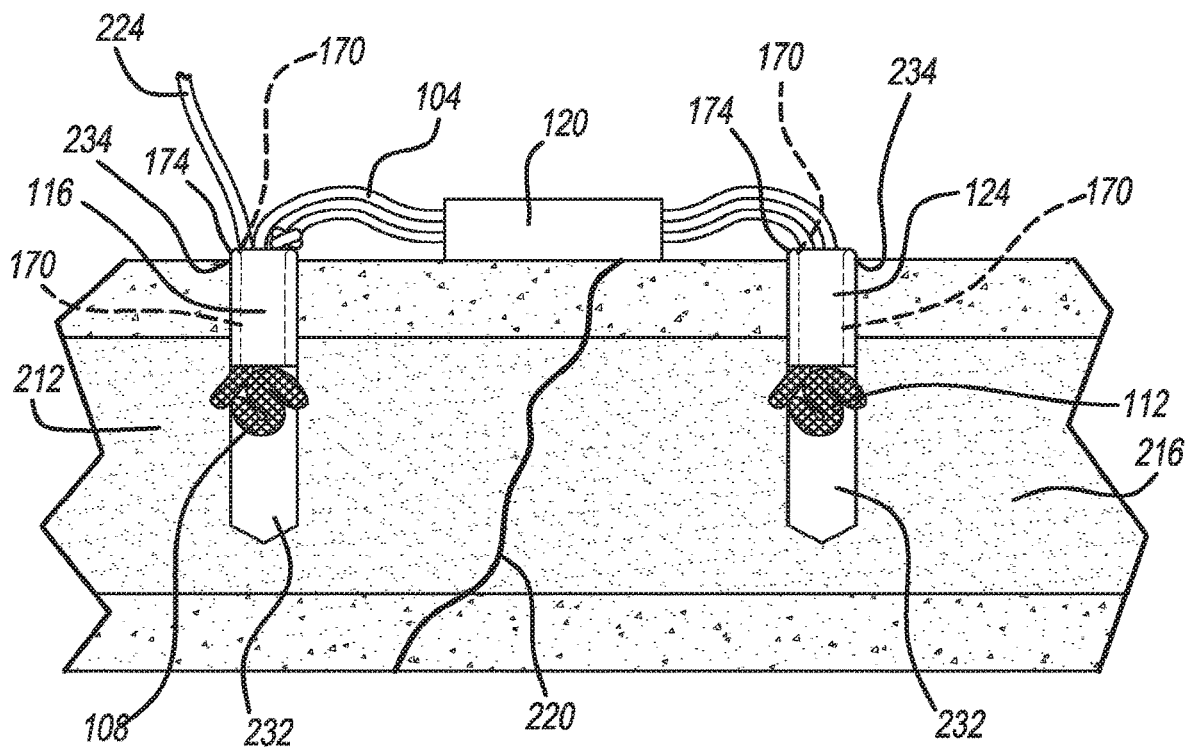
FIG. 12a is an environmental view of the suture construct of FIG. 8 inserted in a fractured bone.

Now referring to FIG. 12a, an illustration of suture assembly 100 in an exemplary fractured bone, such as a metatarsal, is illustrated. Two portions of bone 212, 216 are separated by fracture 220. A bore 232 having an edge 234 is formed into each portion of bone 212, 216, such as by drilling or punching. Suture 104, and, specifically, anchors 108, 112, are inserted into bores 232 using a bone insertion tool as previously described in relation to FIGS. 3-6. In an example embodiment, bores 232 may be blind-bores, extending only partially through the bone. In other embodiments, bores 232 may be through-bores extending through the entire width of the bone. In still other embodiments, one bore may be a blind bore, and another bore may be a through bore.

When flexible anchors 108, 112 are secured within bores 232, end 224 may be pulled to tension the entire suture construct 100. Load distributing elements 116, 124 are inserted and pressed within bores 232 to protect bones 212, 216 from cutting or fracturing from suture 104. Load distributing elements 116, 124 fit snugly within bores 232, ensuring maintenance of proper placement within the bore 232. Load distributing elements 116, 124 may protrude from bores 232 to keep suture 104 from contacting bones 212, 216 along edge 234 of bores 232. As suture 104 enters and exits load distributing elements 116, 124 near edge 234 of bore 232, suture 104 contacts edge 170 and perhaps edge 174 of load distributing elements 116, 124 instead of edge 234 of bore 232 to avoid cutting the bone 212, 216. Edges 170, 174 of load distributing elements 116, 120, 124 are chamfered or rounded to prevent fraying or breaking of suture 104 as force is applied on edges 170, 174 from suture 104.

Load distributing element 120 may be strategically placed on at least one of bone portions 212, 216 to control placement of suture 104 on the bone portions 212, 216 and protect bone portions 212, 216 from damage caused by suture 104. Load distributing elements 116, 120, 124 further protect suture 104 from breaking or fraying caused by bones 212, 216.

As suture construct 100 is tightened, anchors 108, 112 act to retain the suture construct 100 within bone 212, 216. End 224 of suture construct 100 is knotted or a retaining element is inserted to retain the suture construct 100 in place and maintain tension on the suture construct 100. End 224 may either be knotted with itself or knotted with a separate portion of suture 104 in the suture construct 100.

Figure 12B:
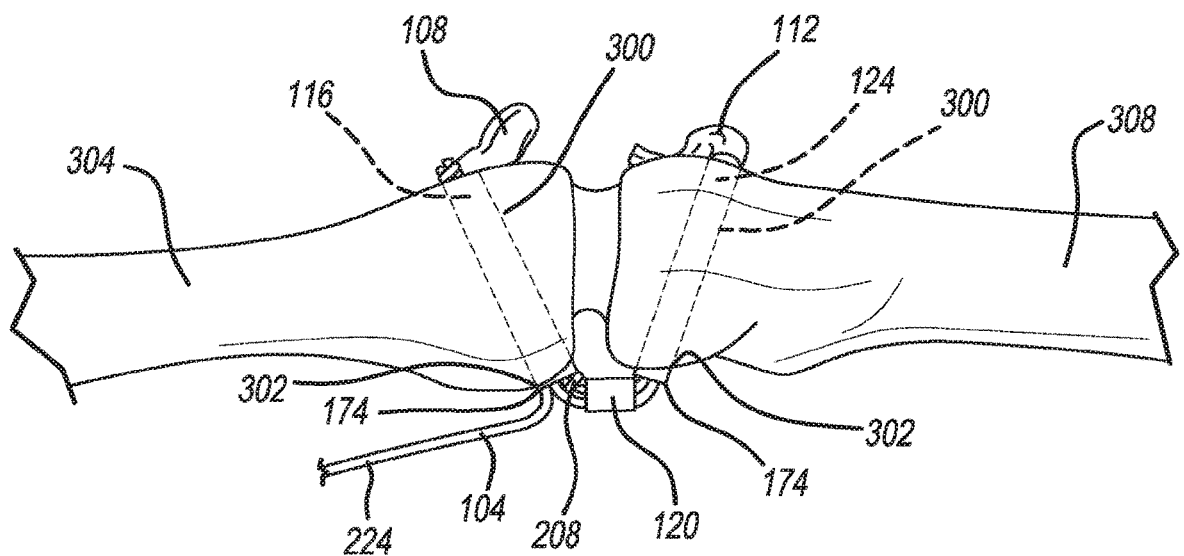
FIG. 12b is an environmental view of the suture construct of FIG. 8 inserted in a plurality of bones.

Now referring to FIG. 12b, an illustration of suture assembly 100 in a plurality of exemplary bones, such as phalanges, is illustrated. A bore 300 having edge 302 is formed into each bone 304, 308, such as by drilling or punching. Suture 104, and, specifically, anchors 108, 112, are inserted into and through bores 300 using a bone insertion tool as previously described in relation to FIGS. 3-6. In an example embodiment, bores 300 may be through-bores extending through the entire width of the bone. In other embodiments, bores 300 may be blind-bores, extending only partially through the bone. In still other embodiments, one bore may be a blind bore, and another bore may be a through bore.

When flexible anchors 108, 112 are secured within bores 300, end 224 may be pulled to tension the entire suture construct 100. Load distributing elements 116, 124 are inserted within bores 300 to protect bones 304, 308 from cutting or fracturing from suture 104. Load distributing elements 116, 124 fit snugly within bores 300, ensuring maintenance of proper placement within the bore 300. Load distributing elements 116, 124 may protrude from bores 300 to keep suture 104 from contacting bones 304, 308 along edge 302 of bores 300. As suture 104 enters and exits load distributing elements 116, 124 near edge 302 of bore 300, suture 104 contacts edge 170 and perhaps edge 174 of load distributing elements 116, 124 instead of edge 302 of bore 300 to avoid cutting the bone 304, 308. Edges 170, 174 of load distributing elements 116, 120, 124 are chamfered or rounded to prevent fraying or breaking of suture 104 as force is applied on edges 170, 174 from suture 104.

Load distributing element 120 may be strategically placed between or on at least one of bones 304, 308 to control placement of suture 104 on the bone 304, 308 and protect bones 304, 308 from damage caused by suture 104. Load distributing elements 116, 120, 124 further protect suture 104 from breaking or fraying caused by bones 212, 216.

As suture construct 100 is tightened, anchors 108, 112 act to retain the suture construct 100 within bone 212, 216. End 224 of suture construct 100 is knotted or a retaining element is inserted to retain the suture construct 100 in place and maintain tension on the suture construct 100. End 224 may either be knotted with itself or knotted with a separate portion of suture 104 in the suture construct 100.

Figure 12C:
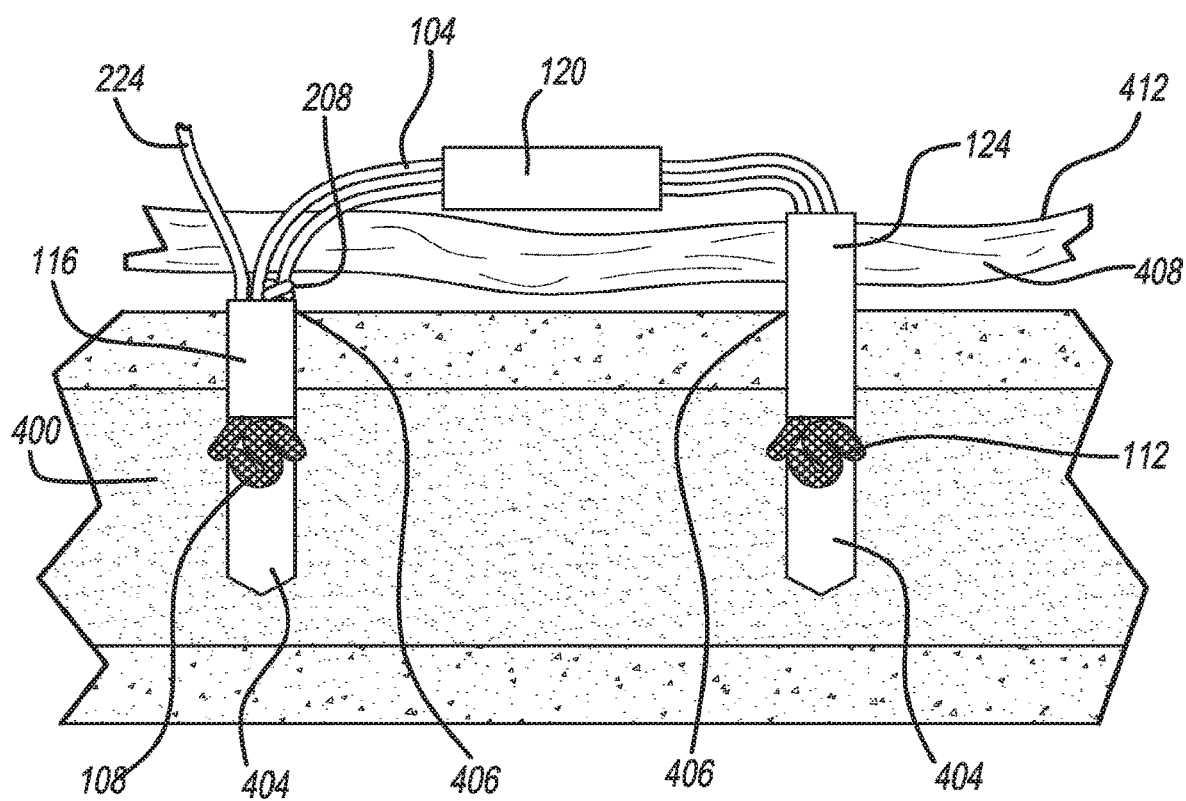
FIG. 12c is an environmental view of the suture construct of FIG. 8 inserted in bone and tissue.

Now referring to FIG. 12c, an illustration of suture assembly 100 in an exemplary bone 400, such as a humerus, for attaching soft tissue such as a rotator cuff is illustrated. A plurality of bores 404 having edges 406 are formed into bone 400, such as by drilling or punching. Suture 104, and, specifically, anchors 108, 112, are inserted into bores 404 using a bone insertion tool 90 as previously described in relation to FIGS. 3-6. In an example embodiment, bores 404 may be blind-bores, extending only partially through the bone. In other embodiments, bores 404 may be through-bores extending through the entire width of the bone. In still other embodiments, one bore may be a blind bore, and another bore may be a through bore.

When flexible anchors 108, 112 are secured within bores 404, end 224 may be pulled to tension the entire suture construct 100. Load distributing elements 116, 124 are inserted and pressed within bores 404 to protect bone 400 from cutting or fracturing from suture 104. Load distributing elements 116, 124 fit snugly within bores 404, ensuring maintenance of proper placement within the bore 404. Load distributing elements 116, 124 may protrude from bores 404 to keep suture 104 from contacting bone 400 along edge 406 of bore 404. As suture 104 enters and exits load distributing elements 116, 124 near edge 406 of bore 404, suture 104 contacts edge 170 and perhaps edge 174 of load distributing elements 116, 124 instead of edge 406 of bore 404 to avoid cutting the bone 400. Edges 170, 174 of load distributing elements 116, 120, 124 are chamfered or rounded to prevent fraying or breaking of suture 104 as force is applied on edges 170, 174 from suture 104.

A portion of soft tissue 408 may be fastened to the bone 400 such as for a rotator cuff repair. The suture 104 may extend from anchor 108, through tissue 408, across tissue 408, back through tissue 408, and through anchor 112. One or both load distributing elements 116, 124 may extend from the bores 404 through the tissue 408 to prevent suture 104 from cutting the tissue 408.

Load distributing element 120 may be strategically placed on a surface 412 of tissue 408 to control placement of suture 104 on tissue 408 and distribute force from suture 104 prevent cutting of tissue. Multiple load distributing elements 120 may be placed along the surface 412 of tissue 408, or the length of load distributing element 120 may be shortened or extended to account for different lengths of suture 104 extending along the surface 412 of tissue 408.

As suture construct 100 is tightened, anchors 108, 112 retain the suture 104 in its position, not allowing suture construct 100 to loosen from its tightened position. Thus, suture construct 100 remains tightened and keeps tissue 408 located on bone 400 for healing.

While a knotted loop has been illustrated in FIGS. 10-12c, it is contemplated that a zip loop of the type disclosed in U.S. Pat. No. 7,601,165, incorporated herein by reference, may also be used.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for securing a flexible member, comprising:
forming a bore in a bone;
inserting a flexible anchor into the bore, the flexible anchor including a passage and being coupled to a flexible member;
slideably positioning a first load distributing member along the flexible member;
inserting the first load distributing member into the bore such that the flexible member engages the first load distributing member; and
applying tension to a portion of the flexible member to secure the flexible anchor and load distributing member within the bone,
wherein the first load distributing member is configured to distribute a load from the flexible member so as to protect bone, soft tissue, or the flexible member.

2. The method of claim 1, wherein the first load distributing member is automatically inserted into the bore when tension is applied to the portion of the flexible member.

3. The method of claim 2, further comprising automatically delivering the first load distributing member into the bore using a retaining element located adjacent to the first load distributing member.

4. The method of claim 1, further comprising placing a second load distributing member on a surface of the bone and distributing the force of the flexible member on the bone.

5. The method of claim 1, further comprising protecting an edge of the bore from the flexible member, wherein the first load distributing member protrudes from the bone and the flexible member engages the first load distributing member to protect the edge.

6. The method of claim 1, further comprising attaching a soft tissue portion to a bone portion using at least one anchor, at least one load distributing member, and the flexible member.

7. The method of claim 1, further comprising pushing the first load distributing member into the bore to snugly engage the first load distributing member within the bore.

8. A method for securing a flexible member comprising:
forming a first bore in a first portion of bone;
forming a second bore in a second portion of bone;
inserting a first flexible anchor into the first bore and a second flexible anchor into the second bore;
positioning a first load distributing element relative to the first bore;
positioning a second load distributing element relative to the second bore, wherein the first and second load distributing elements are slideably engaged to a flexible member; and
applying tension to a portion of the flexible member to secure the first and second load distributing elements and first and second flexible anchors within the first and second bores, respectively.

9. The method of claim 8, further comprising inserting the first and second load distributing elements into the first and second bores, respectively, wherein the first and second load distributing elements fit snugly within the first and second bores.

10. The method of claim 8, further comprising placing a third load distributing member on a surface of at least one of the first and second portions of bone and dispersing the force of the flexible member on the bone.

11. The method of claim 8, further comprising attaching a soft tissue portion to a bone portion using at least one anchor, at least one load distributing member, and the flexible member.

12. The method of claim 8, wherein inserting the first flexible anchor into the first bore and the second flexible anchor into the second bore include deforming the first flexible anchor and the second flexible anchor from a first position to a second position.

13. A method for securing a flexible member, comprising:
slideably positioning a plurality of load distributing members between first and second flexible anchors on a flexible member;
forming first and second bores in a bone;
inserting the first flexible anchor into the first bore;
inserting the second flexible anchor into the second bore; and
applying tension to a portion of the flexible member to secure the first and second flexible anchors and plurality of load distributing members relative to the bone.

14. The method of claim 13, wherein the plurality of load distributing members are configured to distribute at least one load from the flexible member so as to protect bone, soft tissue, or the flexible member.

15. The method of claim 13, further comprising:
positioning at least one of the plurality of load distributing members within the first or second bore.

16. The method of claim 13, wherein at least one of the plurality of load distributing members is formed of a substantially rigid material.

17. The method of claim 13, further comprising:
preventing the plurality of load distributing members from passing over a portion of the flexible member using a retaining element positioned on the flexible member.

18. The method of claim 17, further comprising:
positioning the retaining element on the flexible member near an opening of the first flexible anchor.

* * * * *